United States Patent
Park et al.

(10) Patent No.: US 10,152,574 B2
(45) Date of Patent: Dec. 11, 2018

(54) SIGNAL FEATURE EXTRACTING METHOD AND APPARATUS

(71) Applicant: Samsung Electronics Co., Ltd., Suwon-si (KR)

(72) Inventors: Chang Soon Park, Chungju-si (KR); Ui Kun Kwon, Hwaseong-si (KR); Sang-joon Kim, Hwaseong-si (KR); Seungkeun Yoon, Seoul (KR); Changmok Choi, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/162,982

(22) Filed: May 24, 2016

(65) Prior Publication Data

US 2017/0132384 A1 May 11, 2017

(30) Foreign Application Priority Data

Nov. 9, 2015 (KR) .......................... 10-2015-0156348

(51) Int. Cl.
*G06F 19/00* (2018.01)
*A61B 5/00* (2006.01)
(Continued)

(52) U.S. Cl.
CPC ........ *G06F 19/3418* (2013.01); *A61B 5/0261* (2013.01); *A61B 5/7239* (2013.01);
(Continued)

(58) Field of Classification Search
CPC .............................. G06F 19/3418; H04Q 9/00
See application file for complete search history.

(56) References Cited

U.S. PATENT DOCUMENTS

| 5,785,656 A | * | 7/1998 | Chiabrera | ............ | A61B 8/0875 |
| | | | | | 600/449 |
| 7,074,193 B2 | | 7/2006 | Satoh et al. | | |

(Continued)

FOREIGN PATENT DOCUMENTS

| JP | 2006-43146 A | 2/2006 |
| JP | 2006-102229 A | 4/2006 |

(Continued)

OTHER PUBLICATIONS

European search report issued by the European Patent Office dated Mar. 29, 2017 for the corresponding EP Patent Application No. 16188014.1 (11 pages in English).

(Continued)

*Primary Examiner* — Erin M File
(74) *Attorney, Agent, or Firm* — NSIP Law

(57) ABSTRACT

A signal feature extracting method and apparatus is disclosed. The signal feature extracting apparatus estimates element signals forming an input signal using a signal model to be determined by parameters, and extracts signal features using the estimated element signals. The method of extracting a signal feature including estimating element signals from an input signal, and extracting a signal feature using the estimated element signals, wherein the estimating of the element signals comprises estimating a first element signal of the input signal, and estimating a second element signal based on a waveform of a first intermediate signal, the first intermediate signal being a signal derived from the first element signal eliminated from the input signal.

21 Claims, 18 Drawing Sheets

(51) Int. Cl.
 *A61B 5/026*  (2006.01)
 *H04Q 9/00*  (2006.01)
 *G16H 50/20*  (2018.01)
 *A61B 5/0295*  (2006.01)
 *A61B 5/0452*  (2006.01)
 *A61B 5/11*  (2006.01)
 *A61B 5/1455*  (2006.01)

(52) U.S. Cl.
 CPC .......... *A61B 5/7278* (2013.01); *G06F 19/00* (2013.01); *H04Q 9/00* (2013.01); *A61B 5/0295* (2013.01); *A61B 5/0452* (2013.01); *A61B 5/1102* (2013.01); *A61B 5/14551* (2013.01); *A61B 5/7264* (2013.01); *G16H 50/20* (2018.01)

(56) References Cited

U.S. PATENT DOCUMENTS

| | | | |
|---|---|---|---|
| 8,620,591 B2 | 12/2013 | Wegerich | |
| 8,948,860 B2* | 2/2015 | Causevic | A61B 5/048 600/544 |
| 9,629,564 B2* | 4/2017 | Jonnada | A61B 5/04012 |
| 2007/0149952 A1* | 6/2007 | Bland | G06F 19/345 604/890.1 |
| 2007/0237213 A1* | 10/2007 | Ma | H04B 1/7183 375/219 |
| 2010/0014724 A1 | 1/2010 | Watson et al. | |
| 2013/0023776 A1 | 1/2013 | Olde et al. | |
| 2014/0223462 A1* | 8/2014 | Aimone | H04N 21/42201 725/10 |
| 2015/0182140 A1 | 7/2015 | Ting et al. | |
| 2015/0257645 A1* | 9/2015 | Bae | A61B 5/7225 340/870.07 |
| 2016/0220128 A1* | 8/2016 | Den Brinker | A61B 5/7203 |
| 2016/0291042 A1* | 10/2016 | Kumano | G01N 33/4905 |
| 2016/0331299 A1* | 11/2016 | Cline | A61B 5/746 |
| 2017/0238847 A1* | 8/2017 | Inan | A61B 5/1102 |

FOREIGN PATENT DOCUMENTS

| | | |
|---|---|---|
| KR | 10-1002365 B1 | 12/2010 |
| KR | 10-1210828 B1 | 12/2012 |
| KR | 10-1235441 B1 | 2/2013 |
| KR | 10-1337342 B1 | 12/2013 |
| KR | 10-1503604 B1 | 3/2015 |

OTHER PUBLICATIONS

Banerjee, Rohan, et al. "Noise cleaning and Gaussian modeling of smart phone photoplethysmogram to improve blood pressure estimation." Acoustics, Speech and Signal Processing (ICASSP), 2015 IEEE International Conference on. IEEE, 2015.

James, Christopher J., and Christian W. Hesse. "Independent component analysis for biomedical signals." Physiological measurement 26.1 (2004): R15.

McSharry, Patrick E., et al. "A dynamical model for generating synthetic electrocardiogram signals." IEEE Transactions on Biomedical Engineering 50.3 (2003): 289-294.

Penalver, Antonio, and Francisco Escolano. "Entropy-based incremental variational bayes learning of Gaussian mixtures." IEEE transactions on neural networks and learning systems 23.3 (2012): 534-540.

Xu, Lisheng, et al. "Multi-Gaussian fitting for digital volume pulse using weighted least squares method." Information and Automation (ICIA), 2011 IEEE International Conference on. IEEE, 2011.

* cited by examiner

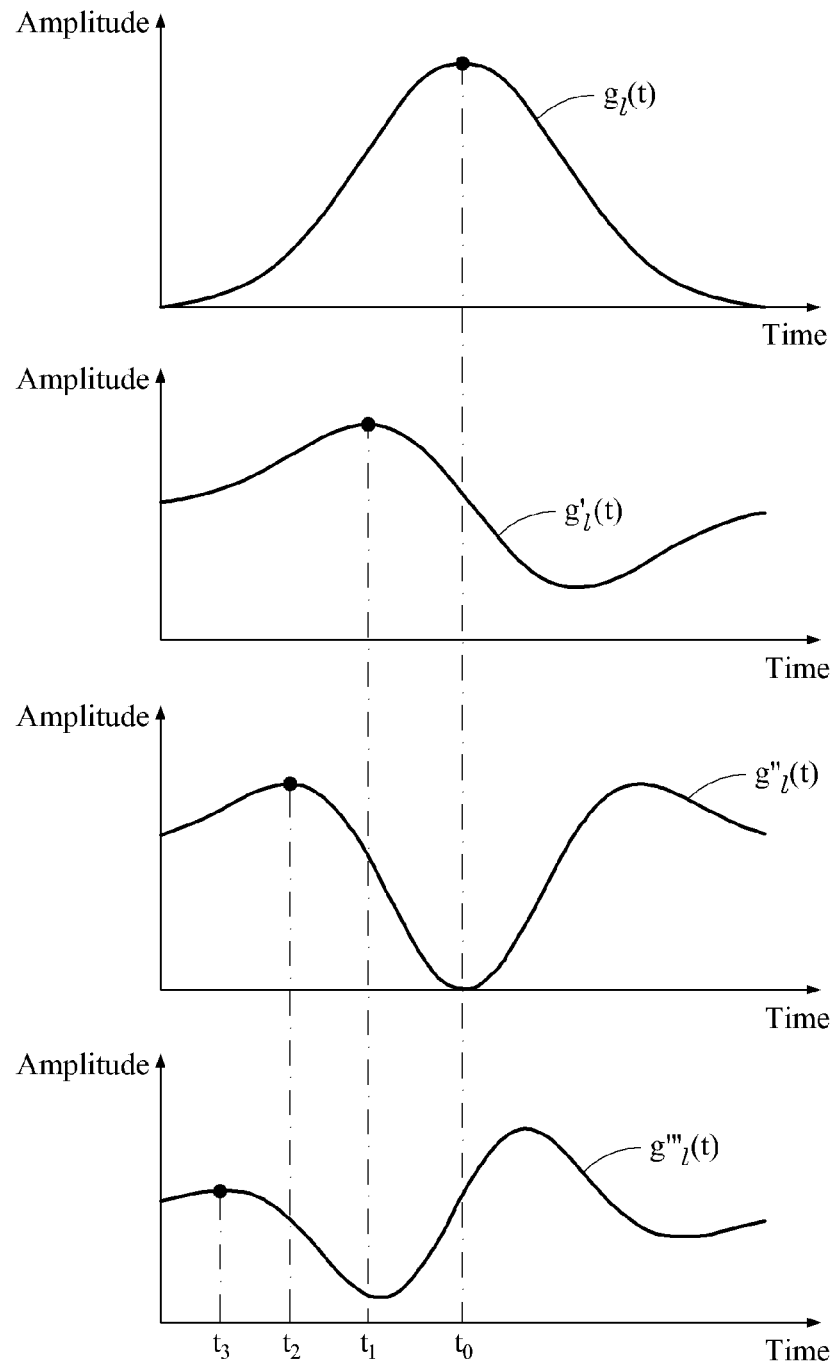

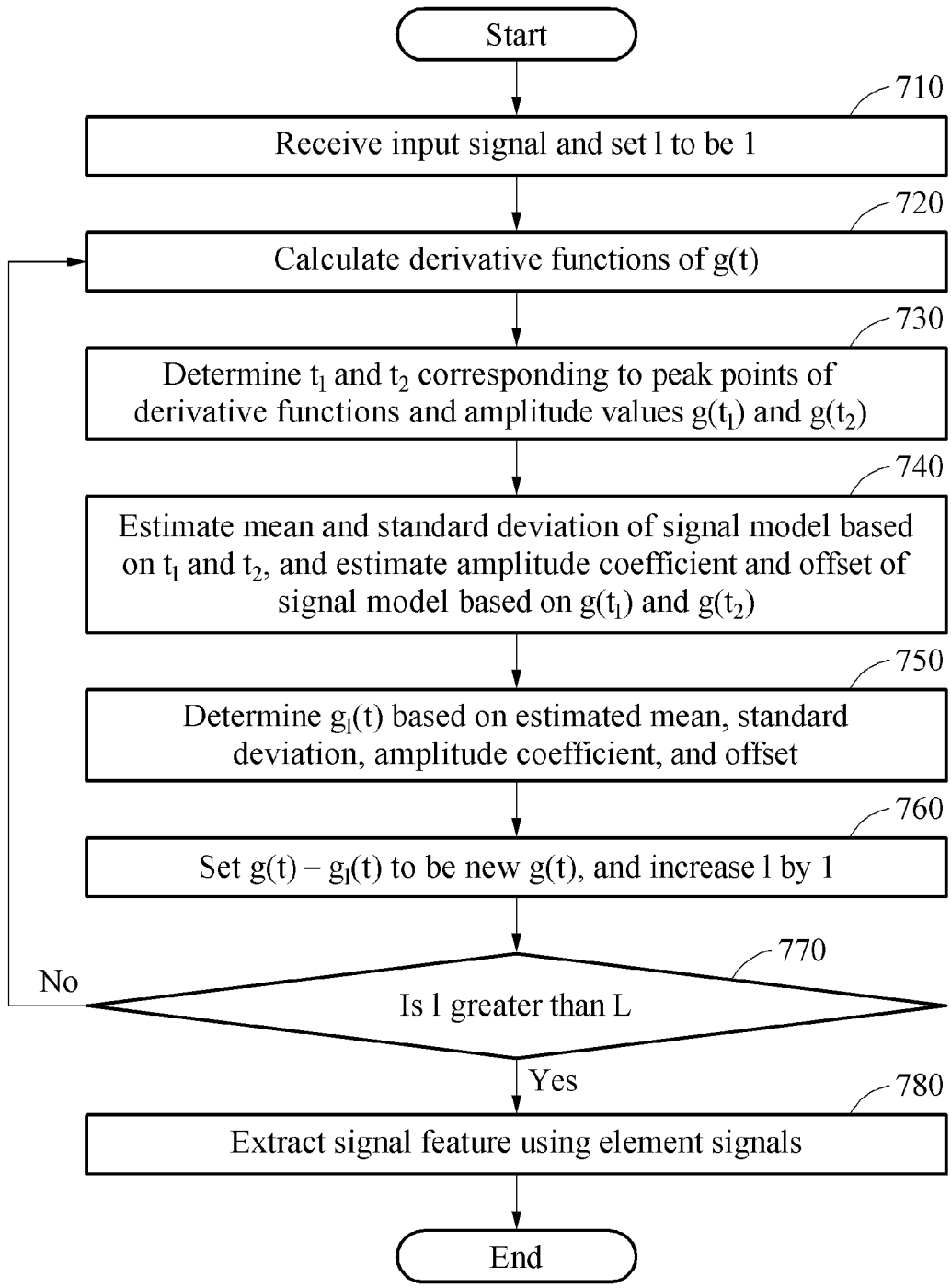

SIGNAL FEATURE EXTRACTING METHOD AND APPARATUS

CROSS-REFERENCE TO RELATED APPLICATION(S)

This application claims the benefit under 35 USC § 119(a) of Korean Patent Application No. 10-2015-0156348 filed on Nov. 9, 2015, in the Korean Intellectual Property Office, the entire disclosure of which is incorporated herein by reference for all purposes.

BACKGROUND

1. Field

The following description relates to technology for extracting a signal feature from an input signal.

2. Description of Related Art

Research is being conducted on information technology (IT)-healthcare convergence technology in which IT is applied to medical technology. Thus, monitoring a health condition of an individual is no longer limited to hospitals, but is now enabled everywhere during the daily life, for example, at home and at work. For example, monitoring a health condition of a user may be enabled through mobile healthcare. In the mobile healthcare, a current health condition of a user may be estimated by measuring a biosignal of the user without restrictions of time and space and analyzing the measured biosignal.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a method of extracting a signal feature, the method including estimating element signals from an input signal, and extracting a signal feature using the estimated element signals, wherein the estimating of the element signals comprises estimating a first element signal of the input signal, and estimating a second element signal based on a waveform of a first intermediate signal, the first intermediate signal being a signal derived from the first element signal eliminated from the input signal.

The estimating of the first element signal may include estimating parameters of the first element signal based on a signal model for modeling the element signals and on a waveform of the input signal, and determining the first element signal by applying the estimated parameters to the signal model.

The estimating of the parameters may include determining derivative signals of different orders by differentiating the waveform of the input signal, and determining the parameters of the first element signal using feature points of the determined derivative signals.

The determining of the parameters may include determining the parameters based on time values corresponding to peak points of the derivative signals and amplitude values of the input signal at the time values.

The estimating of the parameters may include estimating the parameters in a time interval before a peak point of the first element signal.

The estimating of the second element signal may include estimating parameters of the second element signal based on a signal model for modeling the element signals and on the waveform of the first intermediate signal, and determining the second element signal by applying the estimated parameters to the signal model.

The estimating of the parameters may include determining derivative signals of different orders by differentiating the waveform of the first intermediate signal, and determining the parameters of the second element signal using feature points of the determined derivative signals.

The estimating of the second element signal may include determining the first intermediate signal to be the second element signal.

The at least one of the element signals may have a Gaussian waveform.

The signal model may model the waveform of the input signal by overlapping waveforms of the element signals.

The parameters may include a mean, a standard deviation, an amplitude coefficient, and an offset.

The derivative signals may include at least one of a first-order derivative function or a high-order derivative function associated with the waveform of the input signal.

The estimating of the element signals may include estimating a third element signal based on a waveform of a second intermediate signal, the second intermediate signal including the second element signal eliminated from the first intermediate signal.

The estimating of the element signals may include estimating, in sequential order, the element signals based on a signal model for modeling the element signals until a number of element signals are estimated.

The extracting of the signal feature may include extracting at least one of a maximum point, a minimum point, a peak point, an inflection point, a maximum inclination point, a minimum inclination point, and a signal waveform area of the element signals.

In another general aspect, there is provided a method of extracting a signal feature, the method including estimating element signals forming an input signal using a signal model to be determined by parameters, and extracting a signal feature using the estimated element signals.

The estimating of the element signals may include estimating a first element signal of the input signal based on the signal model and on a waveform of the input signal, and estimating a second element signal of the input signal based on a waveform of an intermediate signal, the intermediate signal being a signal derived from removal of the first element signal from the input signal.

In another general aspect, there is provided an apparatus for extracting a signal feature, the apparatus including at least one processor configured to estimate element signals from an input signal, and extract a signal feature using the estimated element signals, and wherein the element signals are estimated based on estimating a first element signal of the input signal, and estimating a second element signal based on a waveform of a first intermediate signal, the first intermediate signal being a signal derived from removal of the first element signal from the input signal.

The element signals may be estimated based on estimating a third element signal based on a waveform of a second intermediate signal, the second intermediate signal including the second element signal is eliminated from the first intermediate signal.

In another general aspect, there is provided an apparatus for extracting a signal feature, the apparatus including a differentiator configured to determine at least one the first-order or higher-order derivative signal from an input signal, a parameter determiner configured to determine parameters of an element sign al based on a signal model for modeling the first-order or higher-order derivative signal and a waveform of the input signal, an element signal estimator configured to estimate the element signal by applying the parameters to the signal model, an intermediate signal determiner configured to determine an intermediate signal by removing the element signal from the input signal, and a feature extractor configured to extract future points from the element signal.

The differentiator may determine another element signal from the intermediate signal, in response to a number of element signals being lesser than a threshold.

The parameters may include at least one of a mean, standard deviation, amplitude coefficient or an offset of the element signal.

Other features and aspects will be apparent from the following detailed description, the drawings, and the claims.

BRIEF DESCRIPTION OF THE DRAWINGS

FIG. 6 is a diagram illustrating an example of an input signal and examples of derivative signals.

FIG. 7 is a diagram illustrating an example of a method of extracting a signal feature.

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1A:
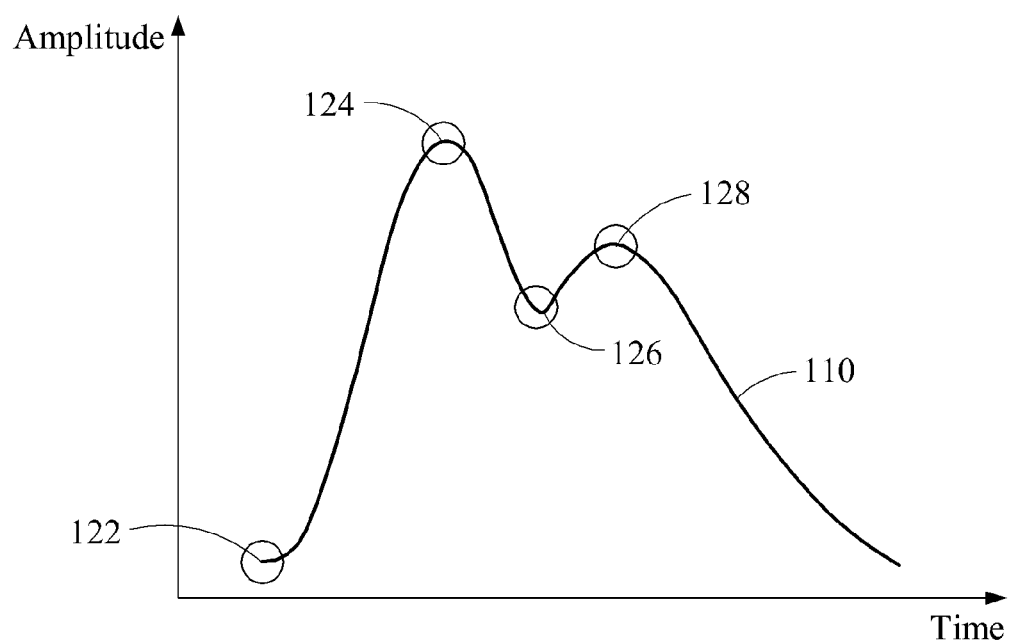
FIGS. 1A through 1E are diagrams illustrating examples of a photoplethysmogram (PPG) signal waveform.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art after a full understanding of the present disclosure. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

The terminology used herein is for the purpose of describing particular examples only, and is not intended to limit the disclosure. As used herein, the singular forms "a," "an," and "the" are intended to include the plural forms as well, unless the context clearly indicates otherwise.

In addition, terms such as first, second, A, B, (a), (b), and the like may be used herein to describe components. Each of these terminologies is not used to define an essence, order, or sequence of a corresponding component but used merely to distinguish the corresponding component from other component(s).

The following examples may be used for monitoring a health condition of a user. Examples may be implemented to monitor a health condition of a user in various forms, such as, for example, a personal computer, a laptop computer, a tablet computer, a mobile device, a smartphone, a television, a smart appliance, a smart vehicle, a wearable device (such as, for example, a ring, a watch, a pair of glasses, glasses-type device, a bracelet, an ankle bracket, a belt, a necklace, an earring, a headband, a helmet, a device embedded in the cloths), a mobile device, a home appliance, content players, communication systems, image processing systems, graphics processing systems, or any other consumer electronics/information technology (CE/IT) device. The following examples may also be implemented in a smart home system, and may be applied to provide healthcare service for the user.

Examples to be described hereinafter may be applied to determine a plurality of element signals forming the input signal and to extract a signal feature using the determined element signals. For convenience of description, the input signal is assumed to be a photoplethysmogram (PPG) signal, and the examples describe extracting a signal feature from a PPG signal. Extracting a signal feature from other types of biosignals, such as, for example, an electrocardiogram (ECG) signal, a ballistocardiogram (BCG) signal, or a blood oxygen saturation level ($SpO_2$) are considered to be well within the scope of the present disclosure.

FIGS. 1A through 1E are diagrams illustrating examples of a PPG signal waveform.

A PPG signal is a biosignal including information on a change in blood flow by a heartbeat. The PPG signal may be of a form in which a propagation wave departs from a heart and moves towards a distal end of a body. The propagation wave overlaps a reflection wave returning to the heart from the distal end of the body. A variety of features associated with a form of the propagation wave or the reflection wave may be extracted from the PPG signal, and cardiovascular information including, for example, a blood pressure, may be estimated based on the extracted features.

In an example, a blood pressure of a user may be estimated by calculating a time difference between a systolic peak point corresponding to a maximum amplitude point of the propagation wave and a diastolic peak point corresponding to a maximum amplitude point of the reflection wave, and dividing a height of the user by the calculated time difference. When a time interval between a point in time at which a propagation wave arrives at a point in a blood vessel and a point in time at which a reflection wave arrives at the point in the blood vessel decreases, a vascular stiffness index tends to increase and a blood pressure tends to increase. Thus, a vascular stiffness index may be estimated based on a time difference between a systolic peak point and a diastolic peak point in a PPG signal, and a blood pressure of a user may be estimated based on the estimated vascular stiffness index. One or more of information relating to a user, such as, for example, vascular stiffness index and blood pressure of the user may be displayed to the user or provided to other components monitoring the health of the user.

FIG. 1A illustrates an example of a portion of a desirable waveform of a PPG signal 110. In the example of FIG. 1A, a horizontal axis indicates a time axis and a vertical axis indicates an amplitude of the PPG signal 110. In the PPG signal 110, a first upward convex portion indicates a waveform component of a propagation wave on the time axis, and a second upward convex portion indicates a waveform component of a reflection wave on the time axis. Although the reflection wave is illustrated as a single reflection wave in FIG. 1A, the reflection wave may be a plurality of reflection waves. A feature point, for example, a feature point 122, a feature point 124, a feature point 126, and a feature point 128 may be significant feature points to derive various sets of information from the waveform of the PPG signal 110. Features correlating with a health condition of a user may be determined using amplitude values or time values of the feature points 122 through 128.

The feature point 126 is also referred to as a dicrotic notch, and corresponds to a point at which a pressure of a blood vessel starts increasing again while decreasing after the feature point 124. The feature point 124 corresponds to a systolic peak point. When such a dicrotic notch is clearly distinguishable in the PPG signal 110, the propagation wave and the reflection wave may be readily distinguished from each other in the PPG signal 110. For example, a point appearing for the second time on a time axis at which a value obtained by differentiating the PPG signal 110 is "0" may be determined to be a dicrotic notch, and the propagation wave and the reflection wave of the PPG signal 110 may be readily distinguished based on the determined dicrotic notch.

However, in an actually measured waveform of a PPG signal, a feature point corresponding to a dicrotic notch may be unclear due to various factors. Thus, a propagation wave and a reflection wave of the PPG signal may not be readily distinguished from each other, and thus an incorrect signal feature may be extracted. FIGS. 1B through 1E illustrate various examples of a PPG signal in which feature points are not clearly distinguishable.

Figure 1B:
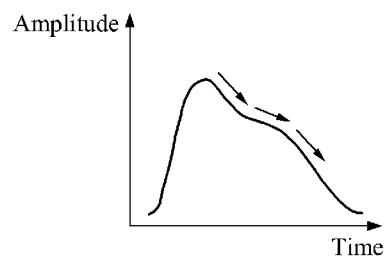
Figure 1C:
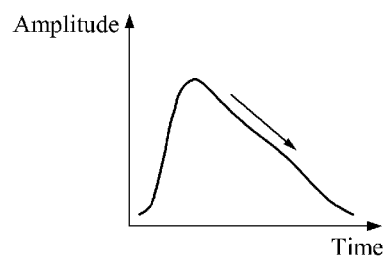
Figure 1D:
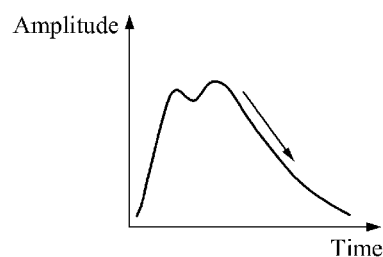
Figure 1E:
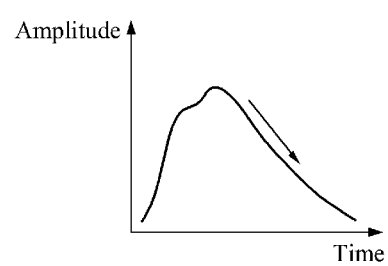

FIGS. 1B and 1O illustrate examples of a waveform of a PPG signal in which a propagation wave and a reflection wave are not readily distinguishable due to an unclear dicrotic notch. FIGS. 1D and 1E illustrate examples of a waveform of a PPG signal in which a maximum value is not indicated in a propagation wave component, but in a reflection wave component. Thus, in FIGS. 1D and 1E, a systolic peak point and a diastolic peak point may be incorrectly determined. As illustrated in FIGS. 1B through 1E, various situations may occur where feature points, such as, for example, systolic peak point or dicrotic notch, are not correctly distinguished from one another in a waveform of a PPG signal. Also, in a waveform of a PPG signal, although a propagation wave may include a single waveform component, a reflection wave may include a plurality of waveforms overlapping one another. In such a case, by distinguishing overlapping waveforms of the reflection wave from the waveform of the PPG signal and analyzing the waveforms, various signal features may be extracted and bioinformation may be more correctly estimated.

A method of extracting a signal feature, hereinafter simply referred to as a signal feature extracting method, and an apparatus for extracting a signal feature, hereinafter simply referred to as a signal feature extracting apparatus, may estimate a plurality of element signals included in an input signal from a waveform of the input signal such as, for example, a PPG signal, and extract a signal feature using the estimated element signals. The signal feature described herein may include feature points such as, for example, a maximum point, a minimum point, a peak point, an inflection point, a maximum inclination point, a minimum inclination point of a signal waveform, or an area of the signal waveform. However, other types of the signal feature are considered to be well within the scope of the present disclosure.

Figure 2:
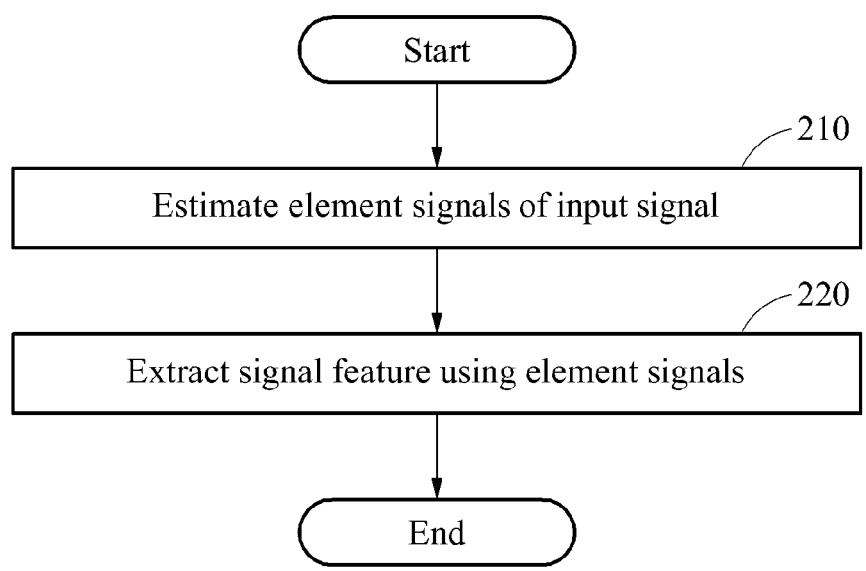
FIGS. 2 and 3 are diagrams illustrating examples of methods of extracting a signal feature.

FIG. 2 is a diagram illustrating an example of a signal feature extracting method. The signal feature extracting method of FIG. 2 is performed by a signal feature extracting apparatus including at least one processor. The operations in FIG. 2 may be performed in the sequence and manner as shown, although the order of some operations may be changed or some of the operations omitted without departing from the spirit and scope of the illustrative examples described. Many of the operations shown in FIG. 2 may be performed in parallel or concurrently. In addition to the description of FIG. 2 below, the above descriptions of FIGS. 1A-1E, are also applicable to FIG. 2, and are incorporated herein by reference. Thus, the above description may not be repeated here.

Referring to FIG. 2, in 210, the signal feature extracting apparatus estimates a plurality of element signals of an input signal. The signal feature extracting apparatus may estimate the element signals based on a signal model for modeling a waveform of the input signal with waveforms of the element signals overlapping one another. The signal feature extracting apparatus may determine parameters for the signal model based on waveform information of the input signal, such as, for example, a change in amplitude over time, and estimate the element signals forming the input signal based on the determined parameters. The signal model may model a form of the input signal in which an element signal has a Gaussian waveform and a plurality of Gaussian waveforms overlap one another. However, a waveform of an element signal is not limited to the Gaussian waveform, and various waveforms of the element signal are considered to be well within the scope of the present disclosure.

The signal feature extracting apparatus may estimate, in sequential order, the element signals from the waveform of the input signal. The signal feature extracting apparatus may estimate an element signal from the waveform of the input signal, generate an intermediate signal by eliminating the estimated element signal from the input signal, and estimate a subsequent element signal from a waveform of the generated intermediate signal. A process of estimating element signals from an input signal by the signal feature extracting apparatus will be described with reference to FIGS. 3 and 4.

In 220, the signal feature extracting apparatus extracts a signal feature using the element signals estimated in 210. For example, the signal feature extracting apparatus may extract, from each element signal, information on a point corresponding to a maximum value and a minimum value, for example, an amplitude and a time, and information on an area of a waveform of an element signal. However, a type of a signal feature to be extracted is not limited to the aforementioned example, and various other types of signal feature may be extracted without departing from the spirit and scope of the illustrative examples described. Based on the extracted signal feature, additional information may be estimated. For example, signal features extracted from a biosignal may be used to estimate information associated with a health condition of a user.

Figure 3:
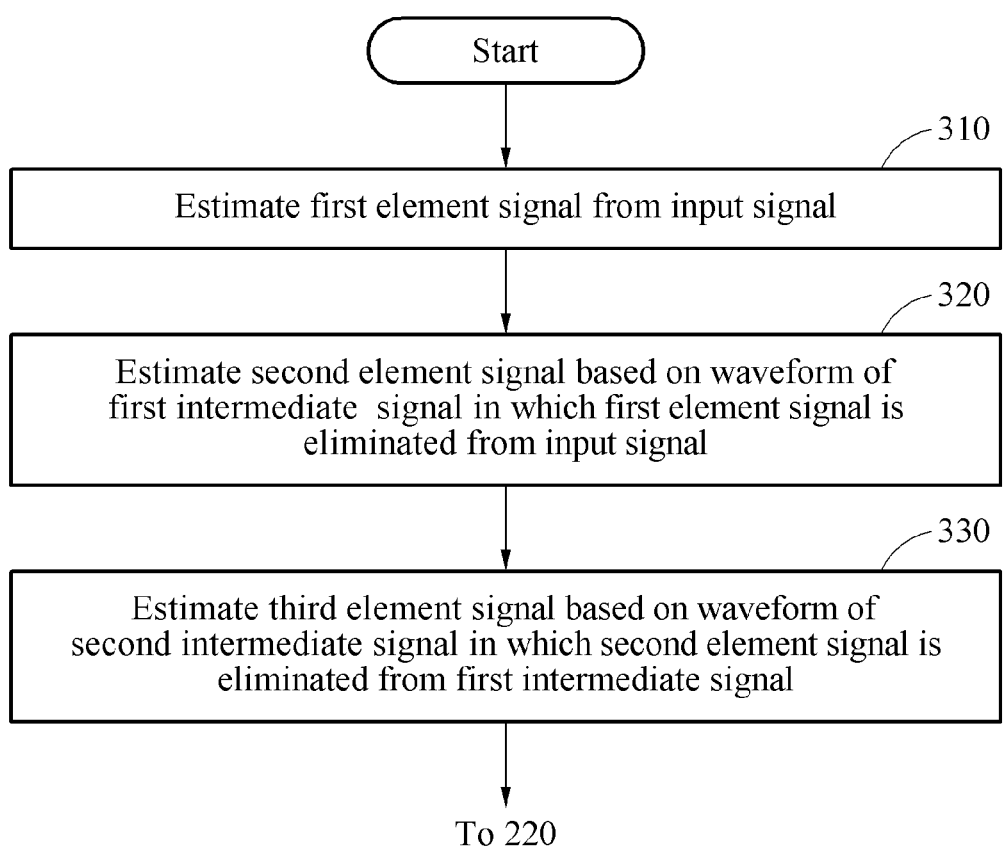

FIG. 3 is a diagram illustrating an example of a process of sequentially estimating element signals. The method of estimating of the element signals of FIG. 3 is performed by a signal feature extracting apparatus including at least one processor. The operations in FIG. 3 may be performed in the sequence and manner as shown, although the order of some operations may be changed or some of the operations omitted without departing from the spirit and scope of the illustrative examples described. Many of the operations shown in FIG. 3 may be performed in parallel or concurrently. In addition to the description of FIG. 3 below, the above descriptions of FIGS. 1A-2, are also applicable to FIG. 3, and are incorporated herein by reference. Thus, the above description may not be repeated here.

Referring to FIG. 3, in 310, a signal feature extracting apparatus estimates a first element signal of an input signal. The signal feature extracting apparatus may estimate parameters of the first element signal based on a signal model for modeling element signals and a waveform of the input signal. The signal feature extracting apparatus may determine derivative signals of different orders by differentiating the waveform of the input signal. The signal feature extracting apparatus may determine the parameters of the first element signal by applying information associated with feature points of the derivative signals to the signal model. The signal feature extracting apparatus may estimate the parameters based on time values corresponding to peak points of the derivative signals and amplitude values of the input signal at the time values. The signal feature extracting apparatus may estimate the parameters in a time interval before a peak point of the first element signal appears. In an example, the signal feature extracting apparatus may determine parameters of an element signal appearing first on a time axis based on the signal model and the waveform of the input signal.

In 320, the signal feature extracting apparatus estimates a second element signal based on a waveform of a first intermediate signal. The first intermediate signal is derived when the first element signal is eliminated from the input signal. The second element signal refers to an element signal appearing subsequent to the first element signal on the time axis. Similar to 310, the signal feature extracting apparatus may determine parameters of the second element signal by determining derivative signals of different orders by differentiating the waveform of the first intermediate signal, and applying information associated with feature points of the determined derivative signals to the signal model. The signal feature extracting apparatus may estimate the parameters in a time interval before a peak point of the second element signal appears. In an example, the signal feature extracting apparatus may determine parameters of an element signal appearing first on the time axis among element signals forming the first intermediate signal based on the signal model and the waveform of the first intermediate signal.

In 330, the signal feature extracting apparatus estimates a third element signal based on a waveform of a second intermediate signal. The second intermediate signal is derived when the second element signal is eliminated from the first intermediate signal. The second intermediate signal refers to a signal in which both the first element signal and the second element signal are eliminated from the input signal. Similar to 320, the signal feature extracting apparatus may determine the third element signal by determining parameters to be applied to the signal model based on the signal model and the waveform of the second intermediate signal, and applying the determined parameters to the signal model. The third element signal may have a same waveform as the first element signal and the second element signal estimated based on the signal model. When the third element signal is a last element signal to be estimated, the second intermediate signal may be determined to be the third element signal without a process of estimating the third element signal using the signal model.

In another example, in operations 310 through 330, the signal feature extracting apparatus may estimate first an element signal appearing last on the time axis. The signal feature extracting apparatus may estimate first an element signal having a waveform with a higher similarity to an entire waveform component.

A process of estimating an element signal from an intermediate signal may be repetitively performed until the number of estimated element signals reaches the number of element signals to be estimated from a waveform of an input signal. For example, when the number of element signals to be estimated from an input signal is "L," the signal feature extracting apparatus may sequentially estimate element signals based on a signal model until L element signals are estimated. In the example of FIG. 3, L is assumed to be 3, and thus the first element signal, the second element signal, and the third element signal are estimated from the input signal. In a case of L being 2, operation 330 may not be performed and operations 310 and 320 may be performed. In such a case, as described in operation 330, the second element signal that is a last element signal may be determined based on the signal model, as in the first element signal, or the first intermediate signal may be determined to be the second element signal.

Figure 4:
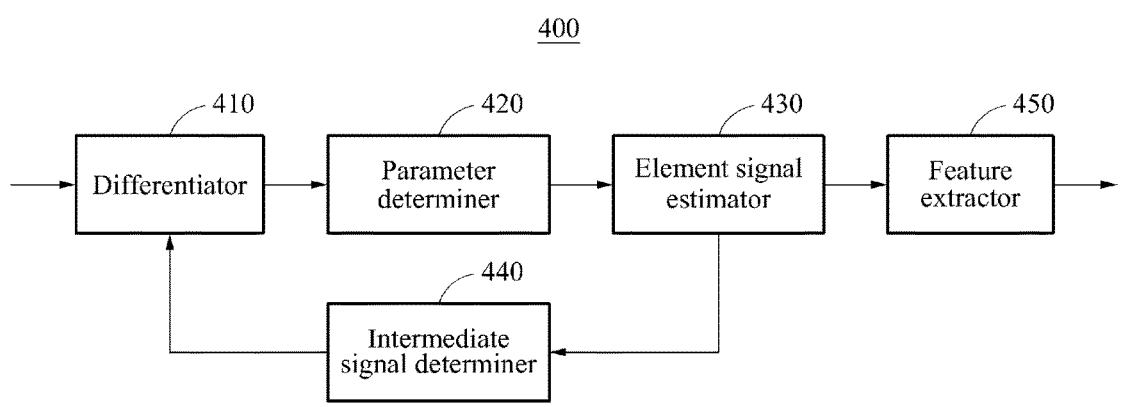
FIG. 4 is a diagram illustrating an example of an apparatus for extracting a signal feature.

FIG. 4 is a diagram illustrating an example of a signal feature extracting apparatus 400. Referring to FIG. 4, the signal feature extracting apparatus 400 includes a differentiator 410, a parameter determiner 420, an element signal estimator 430, an intermediate signal determiner 440, and a feature extractor 450.

The differentiator 410 determines a derivative signal by differentiating a waveform of an input signal. The differentiator 410 determines a first-order derivative signal and a higher-order, for example, a second-order and higher, derivative signal. In an example, noise may be eliminated from the input signal through filtering by a filter (not shown) of the signal feature extracting apparatus 400 before the input signal is input to the differentiator 410. The parameter determiner 420 determines parameters of an element signal to be estimated based on the derivative signal determined by the differentiator 410 and a signal model. The element signal estimator 430 estimates the element signal by applying the parameters determined by the parameter determiner 420 to the signal model. A waveform of an element signal may be determined by various parameters to be applied to the signal model.

The intermediate signal determiner 440 determines an intermediate signal by eliminating, from the input signal, the element signal estimated by the element signal estimator 430. The resulting intermediate signal is input to the differentiator 410, and the differentiator 410 determines a derivative signal by differentiating the intermediate signal. Such a process may be repetitively performed until the preset number of element signals is estimated. For example, the parameter determiner 420 may determine parameters of a subsequent element signal based on the derivative signal and the signal model, and the element signal estimator 430 may estimate the subsequent element signal by applying the determined parameters to the signal model. The intermediate signal determiner 440 may generate another intermediate signal by eliminating the estimated element signal from the previously determined intermediate signal, and the generated intermediate signal may be input to the differentiator 410. When repetition of the process is terminated, a plurality of element signals forming the input signal is determined, and the feature extractor 450 extracts feature points from the determined element signals.

A more detailed description of a process of estimating a plurality of element signals from an input signal using a signal model by the signal feature extracting apparatus 400 will be provided below.

In an example where the number of element signals to be estimated from an input signal is L, and the element signals have a Gaussian waveform, an input signal g(t) in one period, which is formed by L time-shifted Gaussian waveforms overlapping one another, may be expressed as a signal model defined in Equation 1.

$$g(t) = \sum_{l=1}^{L} g_l(t) = \sum_{l=1}^{L} \left( A_l \exp\left(-\frac{(t-m_l)^2}{2\sigma_l^2}\right) + B_l \right) \quad \text{Equation 1}$$

In Equation 1, "g(t)" indicates a signal formed with a sum of L element signals, for example, $g_1(t), g_2(t), \ldots, g_L(t)$. The l-th element signal is indicated by "$g_l(t)$" and "t" denotes a variable indicating a time. A mean of $g_l(t)$ is denoted by "$m_l$," and "$\sigma_l$" denotes a standard deviation of $g_l(t)$. "$A_l$" and "$B_l$" denote an amplitude coefficient and an offset of $g_l(t)$, respectively. The signal feature extracting apparatus 400 may determine waveforms of element signals forming an input signal by determining parameters, for example, $m_l$, $\sigma_l$, $A_l$, and $B_l$ defining $g_l(t)$ in Equation 1 based on an waveform of the input signal.

The signal feature extracting apparatus 400 may determine parameters of an element signal using a derivative function. In Equation 1, Equation 1 may be made irrelevant with regards to the offset $B_l$ by differentiating $g_l(t)$, and may also be made irrelevant with regards to the amplitude coefficient $A_l$ using a time corresponding to a peak value of a derivative function. The signal feature extracting apparatus 400 may determine four parameters for the signal model defining the element signals by estimating the mean $m_l$ and the standard deviation a using derivative functions and estimating the amplitude coefficient $A_l$ and the offset $B_l$ irrespective of the mean $m_l$ and the standard deviation $\sigma_l$. The signal feature extracting apparatus 400 may estimate parameters in a time interval temporally prior to a peak point of each element signal to reduce an error in estimating the parameters, which will be described with reference to FIGS. 5A through 5C.

Figure 5A:
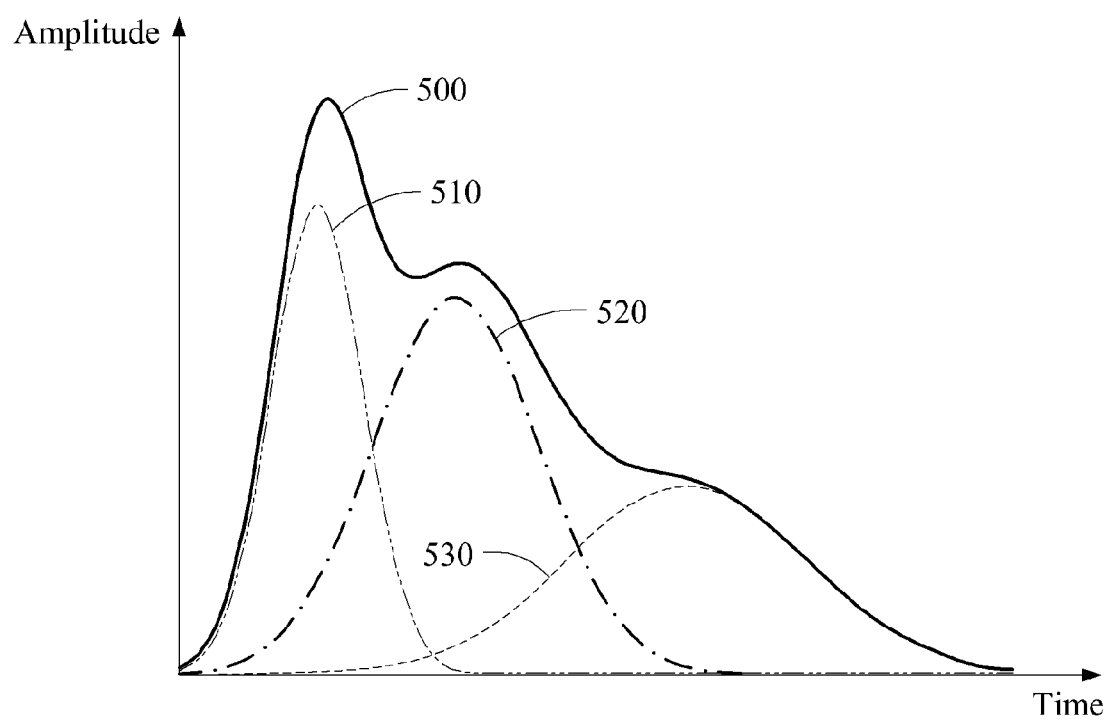
FIGS. 5A through 5C are diagrams illustrating examples of a process of estimating an element signal.

FIG. 5A illustrates an example of a waveform of an input signal 500. In FIG. 5A, the waveforms of three element signals, for example, a first element signal 510, a second element signal 520, and a third element signal 530, overlap one another. The waveform of the input signal 500 may be simply expressed as a sum of the waveforms of the element signals 510 through 530. Referring to FIG. 5A, a front portion of the waveform of the input signal 500 has a higher similarity to the waveform of the first element signal 510. In a front portion on a time axis, amplitudes of the waveforms of the other element signals 520 and 530 are relatively smaller than an amplitude of the waveform of the first element signal 510, and thus the waveform of the input signal 500 and the waveform of the first element signal 510 may be similar to each other.

Figure 5B:
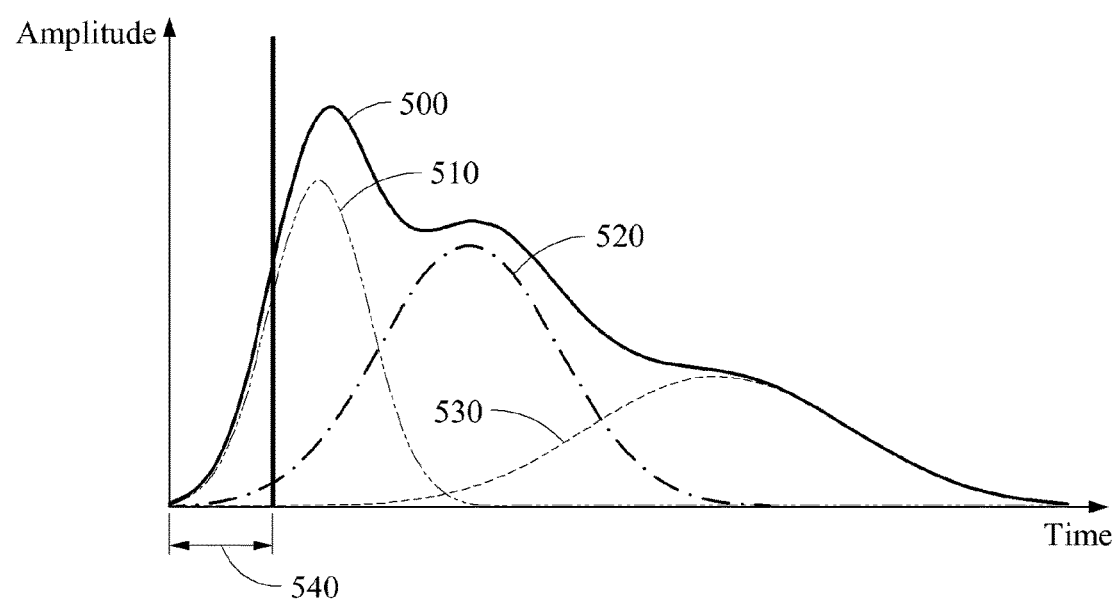
Figure 5C:
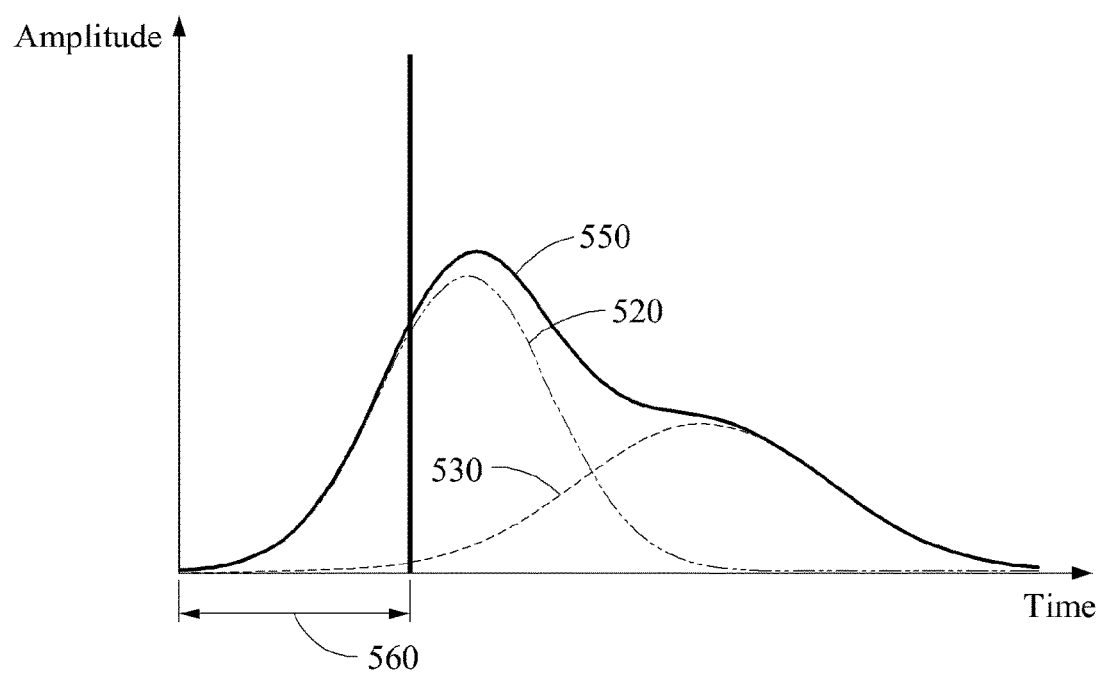

Referring to FIG. 5B, in a time interval 540, the waveform of the input signal 500 is more similar to the waveform of the first element signal 510 than the waveforms of the other element signals 520 and 530. FIG. 5C illustrates an example of a waveform of an intermediate signal 550 in which the first element signal 510 is eliminated from the input signal 500. Referring to FIG. 5C, in a time interval 560, the waveform of the intermediate signal 550 is more similar to the waveform of the second element signal 520 than the waveform of the third element signal 530.

When estimating an element signal occurring temporally earlier to distinguish waveforms of element signals in an input signal, the signal feature extracting apparatus 400 may estimate element signals in a time interval before a peak point of a waveform of each element signal appears to reduce an error in the estimating. Based on the signal model in Equation 1, a time interval prior to a point in time at which a peak point of a waveform of each element signal appears may correspond to $t<m_l$.

Table 1 below indicates time (t) values at respective peak points of an original function $g_l(t)$, a first-order derivative function $g'_l(t)$, a second-order derivative function $g''_l(t)$, and a third-order derivative function $g'''_l(t)$ based on the signal model in Equation 1, in a time interval in which a value of t is smaller than a value of $m_l$.

TABLE 1

| Function | t value at peak point |
|---|---|
| $g_l(t) = A_l \exp\left(-\frac{(t-m_l)^2}{2\sigma_l^2}\right) + B_l$ | $t_0 = m_l$ |
| $g'_l(t) = -A_l \exp\left(-\frac{(t-m_l)^2}{2\sigma_l^2}\right) \cdot \left(\frac{t-m_l}{\sigma_l^2}\right)$ | $t_1 = m_l - \sigma_l$ |
| $g''_l(t) = A_l \exp\left(-\frac{(t-m_l)^2}{2\sigma_l^2}\right) \cdot \left(\left(\frac{t-m_l}{\sigma_l^2}\right)^2 - \frac{1}{\sigma_l^2}\right)$ | $t_2 = m_l - \sqrt{3} \cdot \sigma_l$ |
| $g'''_l(t) = -A_l \exp\left(-\frac{(t-m_l)^2}{2\sigma_l^2}\right) \cdot \left(\left(\frac{t-m_l}{\sigma_l^2}\right)^3 - \frac{3}{\sigma_l^2}\left(\frac{t-m_l}{\sigma_l^2}\right)\right)$ | $t_3 = m_l - \sqrt{3+\sqrt{6}} \cdot \sigma_l$ |

FIG. 6 illustrates examples of signal waveforms corresponding to $g_l(t)$, $g'_l(t)$, $g''_l(t)$, and $g'''_l(t)$, respectively, in Table 1, and t values at peak points. A peak point in a waveform of each derivative signal refers to a point at which an inclination of the waveform is 0, and may be determined in a time interval in which a value of t is smaller than a value of $m_l$.

Referring back to FIG. 4, the differentiator 410 determines two different derivative signals of different orders by differentiating a waveform of an entire signal. The entire signal may correspond to an input signal, or an intermediate signal in which one or more of estimated element signals, such as, for example, first element signal, second element signal, and third element signal are eliminated from the input signal. When a time value is assumed to be a digital sample index, which increases by 1, in a waveform function g(t) of the entire signal, the differentiator 410 may determine a first-order derivative function g'(t) using a relationship of "g'(t)=g(t)−g(t−1)." When expanding such a relationship to an n-th order derivative function $g^{(n)}(t)$, the differentiator 410 may determine the n-th order derivative function using a relationship of "$g^{(n)}(t)=g^{(n-1)}(t)-g^{(n-1)}(t-1)$."

The parameter determiner 420 estimates parameters $m_I$ and $\sigma_I$ of a signal model based on time values at peak points of the determined two derivative signals. In addition, the parameter determiner 420 estimates remaining parameters $A_I$ and $B_I$ based on amplitude values of the input signal at the time values.

When using a first-order derivative function and a second-order derivative function of an entire signal to estimate parameters, the parameter determiner 420 may use a time value, for example, $t_1$ and $t_2$, at a peak point of each derivative function indicated in Table 1. Although the first-order derivative function and the second-order derivative function are provided herein as an example, a scope of examples is not limited thereto. For example, a third-order derivative function or a fourth-order derivative function may be used in lieu of the second-order derivative function, and parameters may be determined based on the third-order derivative function and the fourth-order derivative function.

According to Table 1, when using the first-order derivative function and the second-order derivative function, a relationship between the time values $t_1$ and $t_2$ and the parameters $m_I$ and $\sigma_I$ may be expressed by Equation 2.

$$t_1 = m_I - \sigma_I$$
$$t_2 = m_I - \sqrt{3} \cdot \sigma_I \quad \text{Equation 2:}$$

The parameter determiner 420 determines the parameters $m_I$ and $\sigma_I$ from two linear equations in Equation 2, and the parameters $m_I$ and $\sigma_I$ may be expressed by Equation 3.

$$m_I = \frac{t_1 - t_2}{\sqrt{3} - 1} \quad \text{Equation 3}$$
$$\sigma_I = m_I - t_1$$

The parameter determiner 420 determines the parameters $m_I$ and $\sigma_I$ based on time values corresponding to peak points of derivative functions of different orders as in Equation 3.

The parameter determiner 420 determines the other parameters $A_I$ and $B_I$ using amplitude values $g(t_1)$ and $g(t_2)$ of the entire signal at the time values $t_1$ and $t_2$. A relationship between the amplitude values $g(t_1)$ and $g(t_2)$ and the parameters $A_I$ and $B_I$ may be expressed by Equation 4.

$$g(t_1) \cong g_I(t_1) = A_I \exp\left(-\frac{(t_1 - m_I)^2}{2\sigma_I^2}\right) + B_I = A_I \exp(-1/2) + B_I \quad \text{Equation 4}$$
$$g(t_2) \cong g_I(t_2) = A_I \exp\left(-\frac{(t_2 - m_I)^2}{2\sigma_I^2}\right) + B_I = A_I \exp(-3/2) + B_I$$

In Equation 4, "g(t)" indicates an entire signal in a process of estimating an I-th element signal and indicates, in more detail, a signal in which estimated element signals, for example, $g_1(t), g_2(t), \ldots g_{I-1}(t)$, are eliminated from an initial input signal.

A relationship, for example, $g(t_1) \cong g_I(t_1)$ and $g(t_2) \cong g_I(t_2)$ in Equation 4, may indicate that a waveform of the entire signal g(t) and a waveform of a first element signal $g_I(t)$ are similar to each other in the process of estimating the I-th element signal. The parameter determiner 420 determines the parameters $A_I$ and $B_I$ as in Equation 5 based on Equation 4.

$$A_I = \frac{g_I(t_1) - g_I(t_2)}{\exp(-1/2) - \exp(-3/2)} \quad \text{Equation 5}$$
$$B_I = g_I(t_1) - A_I \exp(-1/2)$$

The element signal estimator 430 determines the I-th element signal by applying the parameters, such as, $m_I$, $\sigma_I$, $A_I$, and $B_I$, which have been determined as in $g_I(t)$ in Equation 1. When the I-th element signal is determined, the intermediate signal determiner 440 generates a new intermediate signal by eliminating the I-th element signal from the entire signal, and the new intermediate signal may be input to the differentiator 410 to be used to estimate an I+1th element signal. Thus, the process described above may be performed iteratively. The process described in the foregoing may be repetitively performed until the a number of element signals is estimated from an input signal. In an example, the number of element signals to be estimated may be preset.

FIG. 7 is a diagram illustrating another example of a signal feature extracting method. The method of estimating of the element signals of FIG. 7 is performed by a signal feature extracting apparatus including at least one processor. The operations in FIG. 7 may be performed in the sequence and manner as shown, although the order of some operations may be changed or some of the operations omitted without departing from the spirit and scope of the illustrative examples described. Many of the operations shown in FIG. 7 may be performed in parallel or concurrently. In addition to the description of FIG. 7 below, the above descriptions of FIGS. 1A-6, are also applicable to FIG. 7, and are incorporated herein by reference. Thus, the above description may not be repeated here.

Referring to FIG. 7, in 710, a signal feature extracting apparatus receives an input signal, and sets a value of I to be 1. Here, "I" indicates an index of an element signal to be estimated. In response to I being 1, the input signal is recognized to be an entire signal g(t). In 720, the signal feature extracting apparatus calculates derivatives functions of different orders by differentiating the entire signal g(t).

In 730, the signal feature extracting apparatus determines time values $t_1$ and $t_2$ corresponding to peak points of the derivative functions and amplitude values $g(t_1)$ and $g(t_2)$. In 740, the signal feature extracting apparatus estimates a mean and a standard derivative of a signal model associated with an I-th element signal $g_I(t)$ by applying the time values $t_1$ and $t_2$ to Equation 3, and estimates an amplitude coefficient and an offset of the signal model by applying the amplitude values $g(t_1)$ and $g(t_2)$ to Equation 5. In 750, the signal feature extracting apparatus determines the I-th element signal $g_I(t)$ based on the estimated mean, standard deviation, amplitude coefficient, and offset. The signal feature extracting apparatus determines the I-th element signal $g_I(t)$ by applying the estimated mean, standard deviation, amplitude coefficient, and offset to the signal model of Equation 1. In 760, the signal feature extracting apparatus sets, to be a new entire signal g(t), a signal in which the I-th element signal $g_I(t)$ is eliminated from the entire signal g(t), and increases the value of I by 1.

In 770, the signal feature extracting apparatus determines whether the value of I is greater than a preset L. In response to the value of I not being greater than L, the signal feature extracting apparatus performs the operations from operation 720 based on the newly set entire signal g(t). The signal feature extracting apparatus repetitively performs 720 through 770 to sequentially estimate a total of L element signals. In operation 780, in response to the value of I being greater than L, the signal feature extracting apparatus extracts a signal feature using the L element signals determined in 710 through 770.

FIGS. 8A through 8D are diagrams illustrating an example of a process of estimating element signals from a waveform of an input signal.

Figure 8A:
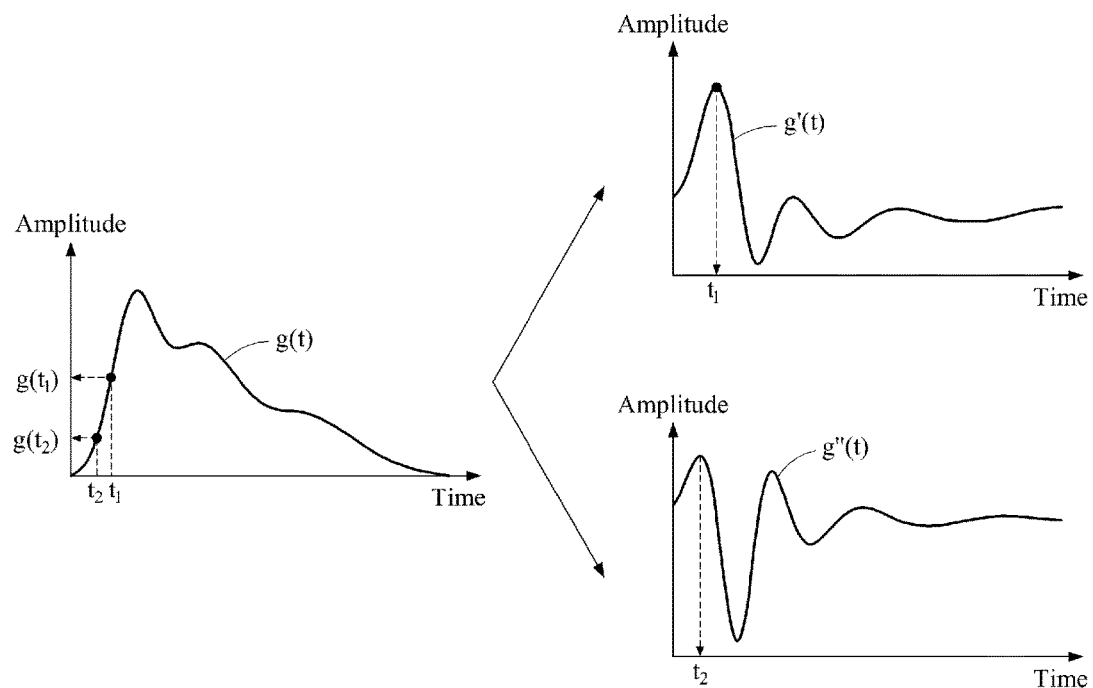
FIGS. 8A through 8D are diagrams illustrating examples of a process of estimating element signals from a waveform of an input signal.

In FIG. 8A, a left graph illustrates a waveform of an input signal g(t), an upper right graph illustrates a waveform of a first-order derivative function g'(t) of g(t), and a lower right graph illustrates a waveform of a second-order derivative function g"(t) of g(t). A signal feature extracting apparatus may determine derivative functions, for example, the first-order derivative function g'(t) and the second-order derivative function g"(t), by differentiating the input signal g(t). The signal feature extracting apparatus may determine time values $t_1$ and $t_2$ for the first maximum points in the first-order derivative function g'(t) and the second-order derivative function g"(t), and determine amplitude values $g(t_1)$ and $g(t_2)$ of the input signal g(t) at the time values $t_1$ and $t_2$.

The signal feature extracting apparatus may determine parameters, a mean and a standard deviation, of a first element signal from Equation 3 based on the time values $t_1$ and $t_2$. In addition, the signal feature extracting apparatus may determine parameters, an amplitude coefficient and an offset, of the first element signal from Equation 5 based on the amplitude values $g(t_1)$ and $g(t_2)$.

Figure 8B:
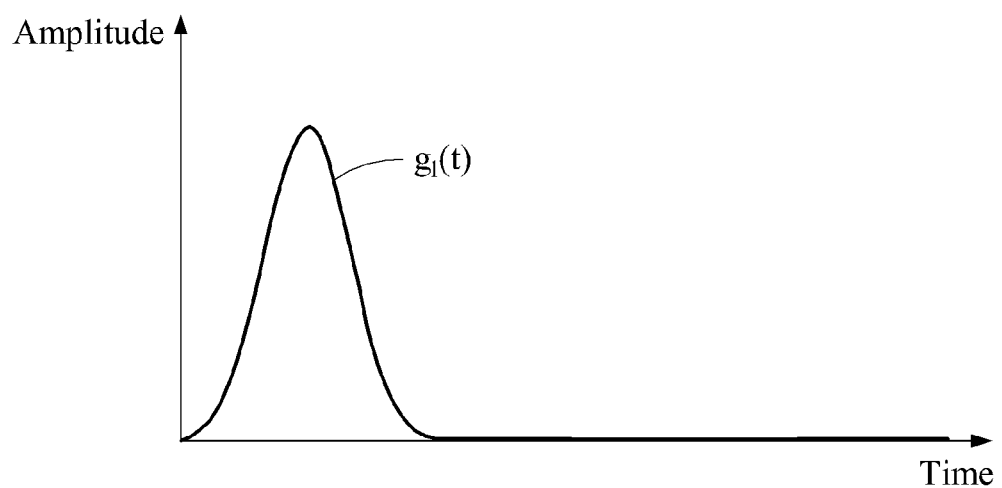

When the mean, standard deviation, amplitude coefficient, and offset are determined in the process described in the foregoing, the first element signal based on the signal model $g_I(t)$ of Equation 1 may be determined. FIG. 8B illustrates an example of a waveform of a first element signal $g_1(t)$ determined in the process described with reference to FIG. 8A.

Figure 8C:
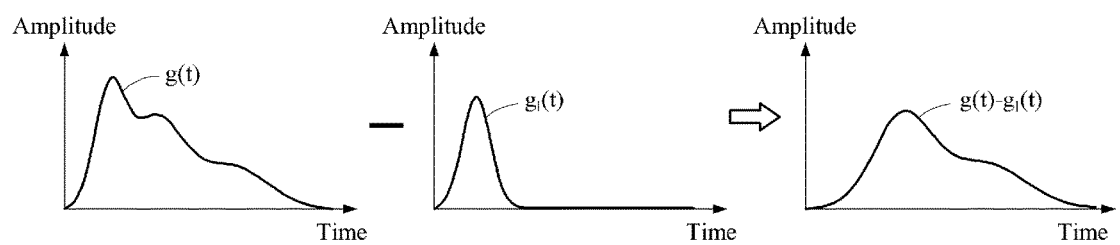

Referring to FIG. 8C, the signal feature extracting apparatus generates an intermediate signal g(t)-$g_1(t)$ illustrated in a right graph by eliminating a waveform of a first element signal $g_1(t)$ illustrated in a middle graph from a waveform of an input signal g(t) illustrated in a left graph. The signal feature extracting apparatus may determine derivative functions of different orders by differentiating the intermediate signal illustrated in the right graph, and estimate a second element signal through the process described above. The signal feature extracting apparatus may repeat the process described above until the preset number of element signals is estimated.

Figure 8D:
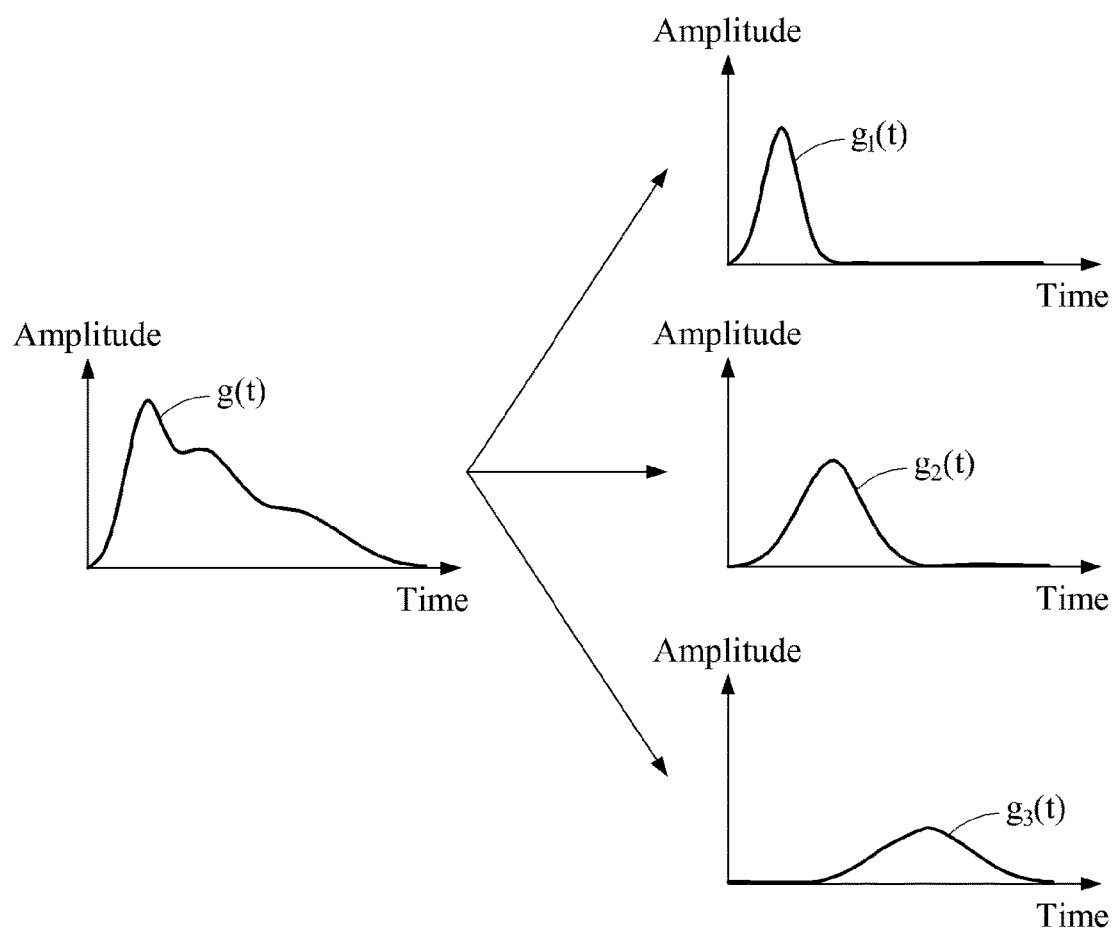

FIG. 8D illustrates an example of a process of determining three element signals from a waveform of an input signal by a signal feature extracting apparatus. A left graph illustrates a waveform of an input signal g(t), and an upper right graph, a right middle graph, and a lower right graph illustrate a waveform of a first element signal $g_1(t)$, a waveform of a second element signal $g_2(t)$, and a waveform of a third element signal $g_3(t)$, respectively. The input signal g(t) may be formed by overlapping the element signals $g_1(t)$, $g^2(t)$, and $g_3(t)$. The signal feature extracting apparatus may extract a feature such as, for example, a maximum point, a minimum point, and a waveform area, from the element signals $g_1(t)$, $g_2(t)$, and $g_3(t)$.

Figure 9A:
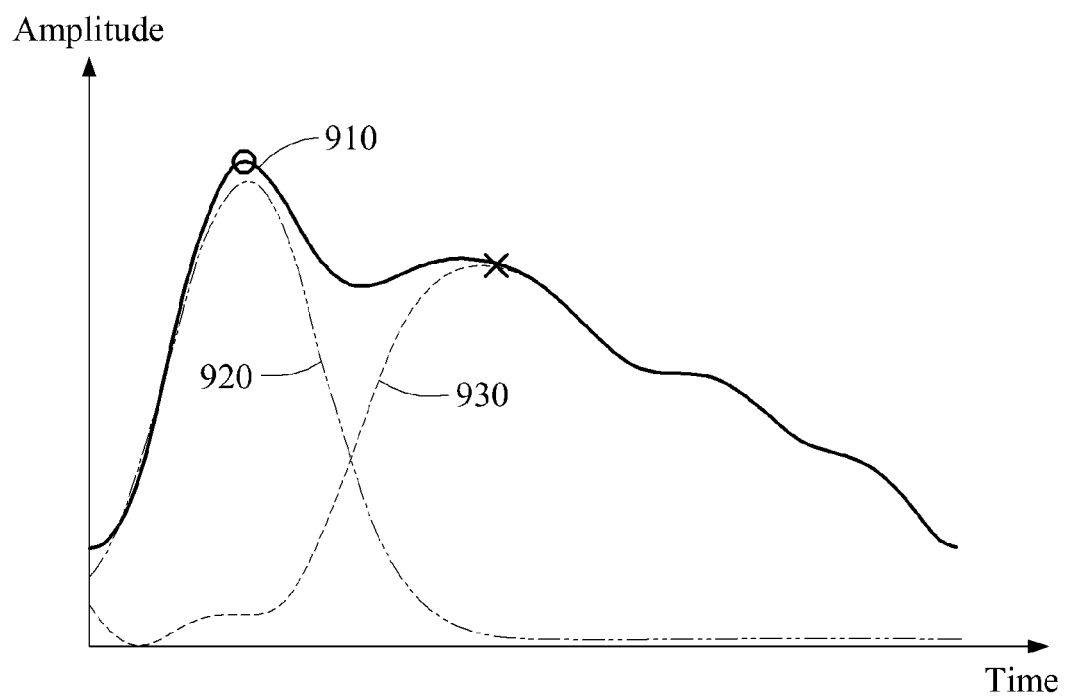
FIGS. 9A through 9C are diagrams illustrating examples of element signals estimated from an input signal.
Figure 9B:
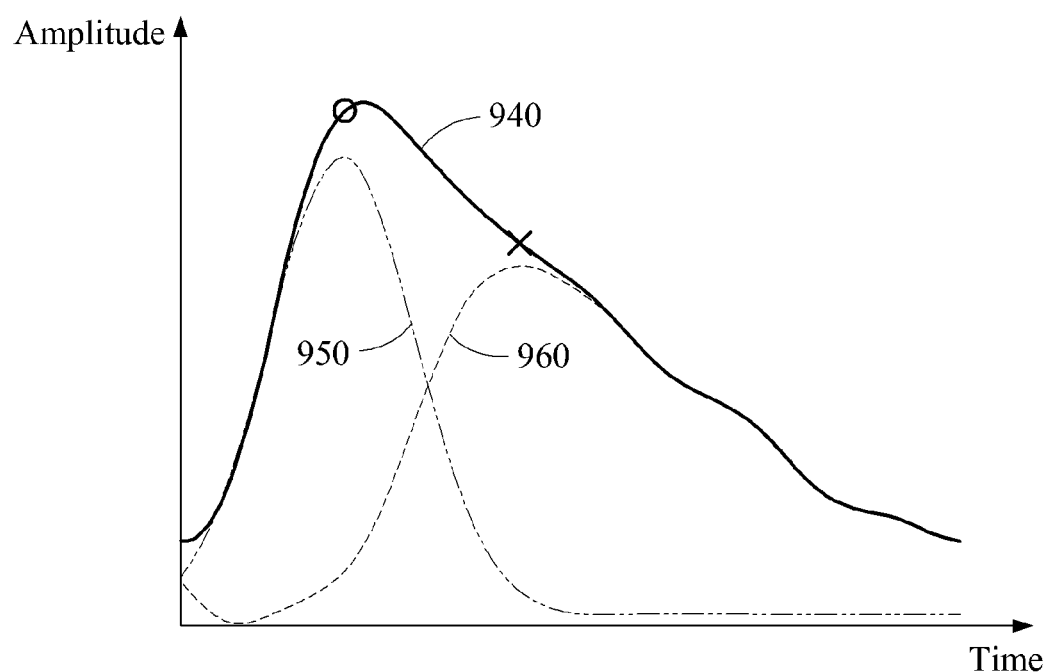
Figure 9C:
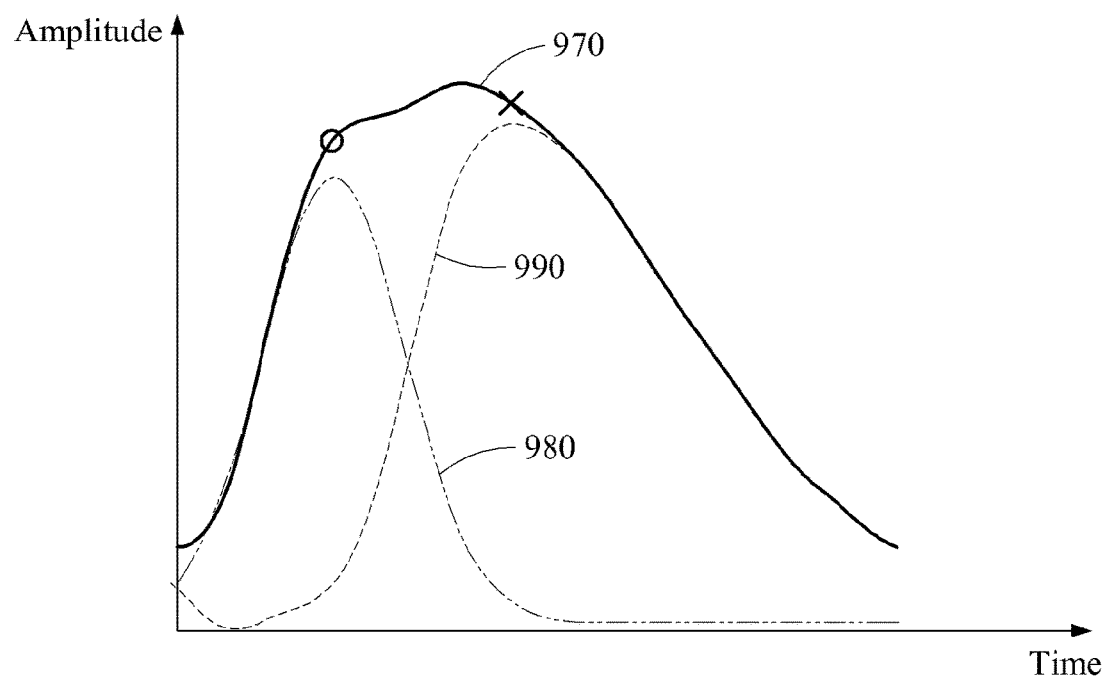

FIGS. 9A through 9C are diagrams illustrating examples of element signals estimated from an input signal. In the examples of FIGS. 9A through 9C, for convenience of explanation, it is assumed that a waveform of an input signal includes waveforms of two element signals. The waveform of an input signal may include other number of element signals, such as, for example two, three, four, or more without departing from the spirit and scope of the illustrative examples described. Here, results of estimating element signals from input signals of different forms by a signal feature extracting apparatus are illustrated.

In the examples of FIGS. 9A through 9C, reference numerals "910," "940," and "970" indicate input signals of different forms, reference numerals "920," "950," and "980" indicate first element signals estimated from respective waveforms of the input signals 910, 940, and 970, and reference numerals "930," "960," and "990" indicate second element signals estimated from the input signals 910, 940, and 970. In an example, a second element signal may include a remaining waveform component in which a first element signal is eliminated from an input signal.

As illustrated in FIGS. 9A through 9C, although an input signal has a waveform with which a feature point of the input signal may not be readily extracted, the signal feature extracting apparatus may determine a plurality of element signals having waveforms with which the feature point of the input signal may be readily extracted from the waveform of the input signal, and thus may readily extract feature points from the determined element signals. In the example of FIG. 9B, in a case of the input signal 940 being a PPG signal, a propagation wave and a reflection wave may not be readily distinguishable from each other due to an unclear feature point of a dicrotic notch in the PPG signal. However, the signal feature extracting apparatus described herein may distinguish the propagation wave and the reflection wave from the input signal 940 using the method described herein. In addition, in the example of FIG. 9C, in a case of the input signal 970 being a PPG signal, an amplitude of a propagation wave is greater than an amplitude of a reflection wave in the PPG signal, and thus a feature point may not be readily extracted from a waveform of the input signal 970. However, the signal feature extracting apparatus may distinguish the propagation wave and the reflection wave from the input signal 970 using the method described herein.

Figure 10:
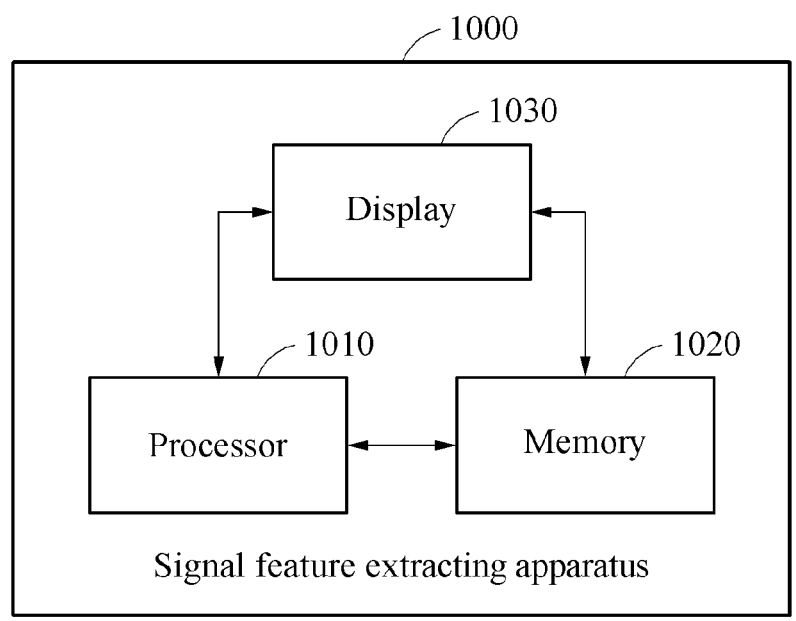
FIG. 10 is a diagram illustrating another example of an apparatus for extracting a signal feature.

FIG. 10 is a diagram illustrating another example of a signal feature extracting apparatus 1000. Referring to FIG. 10, the signal feature extracting apparatus 1000 includes at least one processor 1010, at least one memory 1020, and at least one display 1030.

The processor 1010 performs at least one operation described with reference to FIGS. 1 through 9C. For example, the processor 1010 may estimate a plurality of element signals from an input signal, and extract a signal feature using the estimated element signals. The processor 1010 may be configured as an array of logic gates, the processor 1010 may be configured as hardware of another form without departing from the spirit and scope of the illustrative examples described.

The memory 1020 stores instructions to perform at least one operation described with reference to FIGS. 1 through 9C, or stores data and results obtained during an operation of the signal feature extracting apparatus 1000. In some examples, the memory 1020 may include a non-transitory computer-readable medium, for example, a high-speed random access memory, and/or a nonvolatile computer-readable medium (e.g, at least one disk storage device, flash memory device, and other nonvolatile solid-state memory device).

In an example, the processor 1010 may determine for example, a blood pressure and vascular stiffness index of the user, and may output the sensed blood pressure or vascular stiffness index to a display 1030 of the signal feature extracting apparatus 1000. A display 1030 may be a physical structure that includes one or more hardware components that provide the ability to render a user interface and/or receive user input. The display 1030 can encompass any combination of display region, gesture capture region, a touch sensitive display, and/or a configurable area. The display 1030 can be embedded in the signal feature extracting apparatus 1000 or may be an external peripheral device that may be attached and detached from the signal feature extracting apparatus 1000. The display 1030 may be a single-screen or a multi-screen display. A single physical screen can include multiple displays that are managed as separate logical displays permitting different content to be displayed on separate displays although part of the same physical screen. The display 1030 may also be implemented as an eye glass display (EGD), which includes one-eyed glass or two-eyed glasses.

Although not illustrated in FIG. 10, the signal feature extracting apparatus 1000 may further include an input or output interface, for example, a keyboard, a touch screen, and a microphone, a biometric sensor, or a network communication interface to communicate with an external source. For example, the input or output interface may receive an input from a user or output additional information determined based on a signal feature. The network communication interface may externally transmit information associated with element signals and information associated with an extracted signal feature.

As a non-exhaustive illustration only, the extracting apparatus 400 and 1000 may refer to or be implement in mobile devices such as, for example, a mobile phone, a cellular phone, a smart phone, a wearable smart device (such as, for example, a ring, a watch, a pair of glasses, glasses-type device, a bracelet, an ankle bracket, a belt, a necklace, an earring, a headband, a helmet, a device embedded in the cloths), a personal computer (PC), a laptop, a notebook, a subnotebook, a netbook, or an ultra-mobile PC (UMPC), a tablet personal computer (tablet), a phablet, a mobile internet device (MID), a personal digital assistant (PDA), an enterprise digital assistant (EDA), a digital camera, a digital video camera, a portable game console, an MP3 player, a portable/personal multimedia player (PMP), a handheld e-book, an ultra mobile personal computer (UMPC), a portable lab-top PC, a global positioning system (GPS) navigation, a personal navigation device or portable navigation device (PND), a handheld game console, an e-book, and devices such as a high definition television (HDTV), an optical disc player, a DVD player, a Blue-ray player, a setup box, robot cleaners, a home appliance, content players, communication systems, image processing systems, graphics processing systems, other consumer electronics/information technology (CE/IT) device, or any other device capable of wireless communication or network communication consistent with that disclosed herein. The mobile device may be implemented in a smart appliance, an intelligent vehicle, or in a smart home system.

The mobile device may also be implemented as a wearable device, which is worn on a body of a user. In one example, a wearable device may be self-mountable on the body of the user, such as, for example, a watch, a bracelet, or as an eye glass display (EGD), which includes one-eyed glass or two-eyed glasses. In another non-exhaustive example, the wearable device may be mounted on the body of the user through an attaching device, such as, for example, attaching a smart phone or a tablet to the arm of a user using an armband, incorporating the wearable device in a cloth of the user, or hanging the wearable device around the neck of a user using a lanyard.

The apparatuses, units, modules, devices, and other components illustrated in FIGS. 4 and 10 that perform the operations described herein with respect to FIGS. 2, 3, and 5A-9C are implemented by hardware components. Examples of hardware components include controllers, sensors, generators, drivers, memories, comparators, arithmetic logic units, adders, subtractors, multipliers, dividers, integrators, and any other electronic components known to one of ordinary skill in the art. In one example, the hardware components are implemented by computing hardware, for example, by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 2, 3, and 5A-9C. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 2, 3, and 5A-9C that perform the operations described herein are performed by computing hardware as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of extracting a signal feature, the method comprising:
   estimating element signals comprising a first element signal having a higher similarity to the input signal compared to other element signals, a second element signal, and a third element signal, that form an input signal;
   estimating the first element signal in a time interval before a peak point of a waveform of the input signal;
   generating a first intermediate signal by removing the first element signal from the input signal;
   estimating the second element signal based on a waveform of the first intermediate signal;
   generating a second intermediate signal by removing the second element signal from the first intermediate signal;
   estimating the third element signal based on a waveform of the second intermediate signal;
   extracting a signal feature using the estimated first element signal and the estimated second element signal;
   estimating health parameters using the extracted signal feature; and
   displaying the health parameters on a screen comprising a gesture capture region and separate logical displays each permitting different content to be displayed.

2. The method of claim 1, wherein the estimating of the first element signal comprises:
   estimating parameters of the first element signal based on a signal model for modeling the element signals and on a waveform of the input signal; and
   determining the first element signal by applying the estimated parameters to the signal model.

3. The method of claim 2, wherein the estimating of the parameters comprises:
   determining derivative signals of different orders by differentiating the waveform of the input signal; and
   determining the parameters of the first element signal using feature points of the determined derivative signals.

4. The method of claim 3, wherein the determining of the parameters comprises:
   determining the parameters based on time values corresponding to peak points of the derivative signals and amplitude values of the input signal at the time values.

5. The method of claim 2, wherein the estimating of the parameters comprises:
   estimating the parameters in a time interval before a peak point of the first element signal.

6. The method of claim 1, wherein the estimating of the second element signal comprises:
   estimating parameters of the second element signal based on a signal model for modeling the element signals and on the waveform of the first intermediate signal; and
   determining the second element signal by applying the estimated parameters to the signal model.

7. The method of claim 6, wherein the estimating of the parameters comprises:
   determining derivative signals of different orders by differentiating the waveform of the first intermediate signal; and
   determining the parameters of the second element signal using feature points of the determined derivative signals.

8. The method of claim 1, wherein the estimating of the second element signal comprises:
   determining whether or not the first intermediate signal is the second element signal, based on whether the second element signal is a last signal to be estimated.

9. The method of claim 1, wherein at least one of the first or second element signals has a Gaussian waveform.

10. The method of claim 2, wherein the signal model models the waveform of the input signal by overlapping waveforms of the element signals.

11. The method of claim 2, wherein the parameters comprise a mean, a standard deviation, an amplitude coefficient, and an offset.

12. The method of claim 3, wherein the derivative signals comprise at least one of a first-order derivative function or a higher-order derivative function associated with the waveform of the input signal.

13. The method of claim 1, wherein the estimating of the element signals comprises:
estimating, in sequential order, the element signals based on a signal model for modeling the element signals until a number of element signals are estimated.

14. The method of claim 1, wherein the extracting of the signal feature comprises:
extracting at least one of a maximum point, a minimum point, a peak point, an inflection point, a maximum inclination point, a minimum inclination point, and a signal waveform area of the element signals.

15. A non-transitory computer-readable storage medium storing instructions to cause computing hardware to perform the method of claim 1.

16. A method of extracting a signal feature, the method comprising:
estimating element signals, comprising a first element signal having a higher similarity to the input signal compared to other element signals, a second element signal, and a third element signal, included in an input signal using a signal model to be determined by parameters;
estimating the first element signal in a time interval before a peak point of a waveform of the input signal;
generating a first intermediate signal by removing the first element signal;
estimating the second element signal based on a waveform of the first intermediate signal;
generating a second intermediate signal by removing the second element signal from the first intermediate signal;
estimating the third element signal based on a waveform of the second intermediate signal;
extracting a signal feature using the estimated first element signal and the estimated second element signal;
estimating health parameters using the extracted signal feature; and
displaying the health parameters on a screen comprising a gesture capture region and separate logical displays each permitting different content to be displayed.

17. The method of claim 16, wherein the estimating of the element signals comprises:
estimating a first element signal of the input signal based on the signal model and on a waveform of the input signal.

18. An apparatus for extracting a signal feature, the apparatus comprising:
at least one processor configured to:
estimate element signals, comprising a first element signal having a higher similarity to the input signal compared to other element signals, a second element signal, and a third element signal, from an input signal;
estimate the first element signal in a time interval before a peak point of a waveform of the input signal;
generate a first intermediate signal by removing the first element signal from the input signal;
estimate the second element signal based on a waveform of the first intermediate signal;
generate a second intermediate signal by removing the second element signal from the first intermediate signal;
estimate the third element signal based on a waveform of the second intermediate signal;
extract a signal feature using the estimated first element signal and the estimated second element signal;
estimate health parameters using the extracted signal feature; and
display the health parameters on a screen; and
a screen comprising a gesture capture region and separate logical displays each permitting different content to be displayed.

19. An apparatus for extracting a signal feature, the apparatus comprising:
a differentiating hardware processor configured to determine at least one of a first-order or higher-order derivative signal from an input signal;
a parameter determining hardware processor configured to determine parameters of an element signal having a higher similarity to the input signal compared to other element signals from the input signal based on a signal model for modeling the first-order or higher-order derivative signal and a waveform of the input signal;
an element signal estimating hardware processor configured to estimate the element signal by applying the parameters to the signal model in a time interval before a peak point of a waveform of the input signal, to estimate a second element signal and a third element signal;
an intermediate signal determining hardware processor configured to:
generate a first intermediate signal by removing the first element signal from the input signal, and
generate a second intermediate signal be removing the second element signal from the first intermediate signal, wherein the element signal estimating hardware processor is configured to estimate the second element signal based on a waveform of the first intermediate signal and estimate the third element signal based on a waveform of the second intermediate signal;
a feature extracting hardware processor configured to extract feature points from the element signal; and
one or more processors configured to estimate health parameters using the extracted signal feature and display the health parameters on a screen; and
a screen comprising a gesture capture region and separate logical displays each permitting different content to be displayed.

20. The apparatus of claim 19, wherein the differentiating hardware processor is further configured to determine another element signal from the intermediate signal, in response to a number of element signals being lesser than a threshold.

21. The apparatus of claim 19, wherein the parameters comprise at least one of a mean, standard deviation, amplitude coefficient, or an offset of the element signal.

* * * * *